(12) United States Patent
Takii

(10) Patent No.: US 12,133,687 B2
(45) Date of Patent: Nov. 5, 2024

(54) OPHTHALMIC APPARATUS

(71) Applicant: NIDEK CO., LTD., Aichi (JP)

(72) Inventor: Michihiro Takii, Aichi (JP)

(73) Assignee: NIDEK CO., LTD., Aichi (JP)

( * ) Notice: Subject to any disclaimer, the term of this patent is extended or adjusted under 35 U.S.C. 154(b) by 691 days.

(21) Appl. No.: 17/215,327

(22) Filed: Mar. 29, 2021

(65) Prior Publication Data

US 2021/0298599 A1 Sep. 30, 2021

(30) Foreign Application Priority Data

Mar. 30, 2020 (JP) ................................. 2020-060070
Mar. 30, 2020 (JP) ................................. 2020-060071
Mar. 30, 2020 (JP) ................................. 2020-060072

(51) Int. Cl.
*A61B 3/14* (2006.01)
*A61B 3/00* (2006.01)
(Continued)

(52) U.S. Cl.
CPC .............. *A61B 3/18* (2013.01); *A61B 3/0025* (2013.01); *A61B 3/0091* (2013.01); *A61B 3/1005* (2013.01); *A61B 3/102* (2013.01); *A61B 3/103* (2013.01); *A61B 3/1035* (2013.01); *A61B 3/107* (2013.01); *A61B 3/117* (2013.01); *A61B 3/1173* (2013.01); *A61B 3/12* (2013.01); *A61B 3/1225* (2013.01); *A61B 3/14* (2013.01)

(58) Field of Classification Search
CPC ....... A61B 3/18; A61B 3/0025; A61B 3/0091; A61B 3/1005; A61B 3/102; A61B 3/103; A61B 3/1035; A61B 3/107; A61B 3/117; A61B 3/1173; A61B 3/12; A61B 3/1225; A61B 3/14

USPC .......................................................... 351/206
See application file for complete search history.

(56) References Cited

U.S. PATENT DOCUMENTS

2007/0097317 A1 5/2007 Hayashi et al.
2013/0021577 A1 1/2013 Suzuki et al.
(Continued)

FOREIGN PATENT DOCUMENTS

EP 3 210 526 A1 8/2017
EP 3 639 727 A2 4/2020
(Continued)

OTHER PUBLICATIONS

Search Report issued Aug. 17, 2021 by the European Patent Office in counterpart European Patent Application No. 21165538.6.
(Continued)

*Primary Examiner* — Mahidere S Sahle
(74) *Attorney, Agent, or Firm* — Sughrue Mion, PLLC

(57) ABSTRACT

An ophthalmic apparatus includes a first optical system for acquiring information regarding an eye refractive power of a subject eye based on reflection light of measurement light reflected from a fundus of the subject eye, a second optical system for acquiring anterior segment information regarding a shape of an anterior segment of the subject eye, and a calculation controller that acquires an axial length of the subject eye based on an on-surface eye refractive power, which is the eye refractive power on a cross section on which an optical axis of the first optical system is arranged and the anterior segment information regarding the cross section.

17 Claims, 8 Drawing Sheets

(51) Int. Cl.
   *A61B 3/10*     (2006.01)
   *A61B 3/103*    (2006.01)
   *A61B 3/107*    (2006.01)
   *A61B 3/117*    (2006.01)
   *A61B 3/12*     (2006.01)
   *A61B 3/18*     (2006.01)

(56) References Cited

U.S. PATENT DOCUMENTS

| | | |
|---|---|---|
| 2013/0100408 A1 | 4/2013 | Simpson |
| 2013/0235343 A1 | 9/2013 | Hee et al. |
| 2015/0221125 A1* | 8/2015 | Shimizu ............... A61B 3/1005 382/128 |
| 2017/0245756 A1 | 8/2017 | Hayashi et al. |
| 2020/0100673 A1* | 4/2020 | Shimizu ............... A61B 3/1225 |
| 2020/0100674 A1 | 4/2020 | Yamanari et al. |

FOREIGN PATENT DOCUMENTS

| | | |
|---|---|---|
| JP | 63-197432 A | 8/1988 |
| JP | 2-295538 A | 12/1990 |
| JP | 2001-269314 A | 10/2001 |
| JP | 2004-8768 A | 1/2004 |
| JP | 2007-144128 A | 6/2007 |
| JP | 2008-188047 A | 8/2008 |
| JP | 2009-56149 A | 3/2009 |
| JP | 2012-115575 A | 6/2012 |
| JP | 2012-224621 A | 11/2012 |
| JP | 2012-249768 A | 12/2012 |
| JP | 2013-6101 A | 1/2013 |
| JP | 2014-198277 A | 10/2014 |
| JP | 2014-534004 A | 12/2014 |
| JP | 2015-509433 A | 3/2015 |
| JP | 2016-220860 A | 12/2016 |
| JP | 2019-13392 A | 1/2019 |
| JP | 2019-63044 A | 4/2019 |
| JP | 2020-31827 A | 3/2020 |

OTHER PUBLICATIONS

Communication issued on Sep. 5, 2023 by the Japanese Patent Office for Japanese Patent Application No. 2020-060070.
Communication issued on Sep. 5, 2023 by the Japanese Patent Office for Japanese Patent Application No. 2020-060071.
Communication issued on Sep. 5, 2023 by the Japanese Patent Office for Japanese Patent Application No. 2020-060072.

* cited by examiner

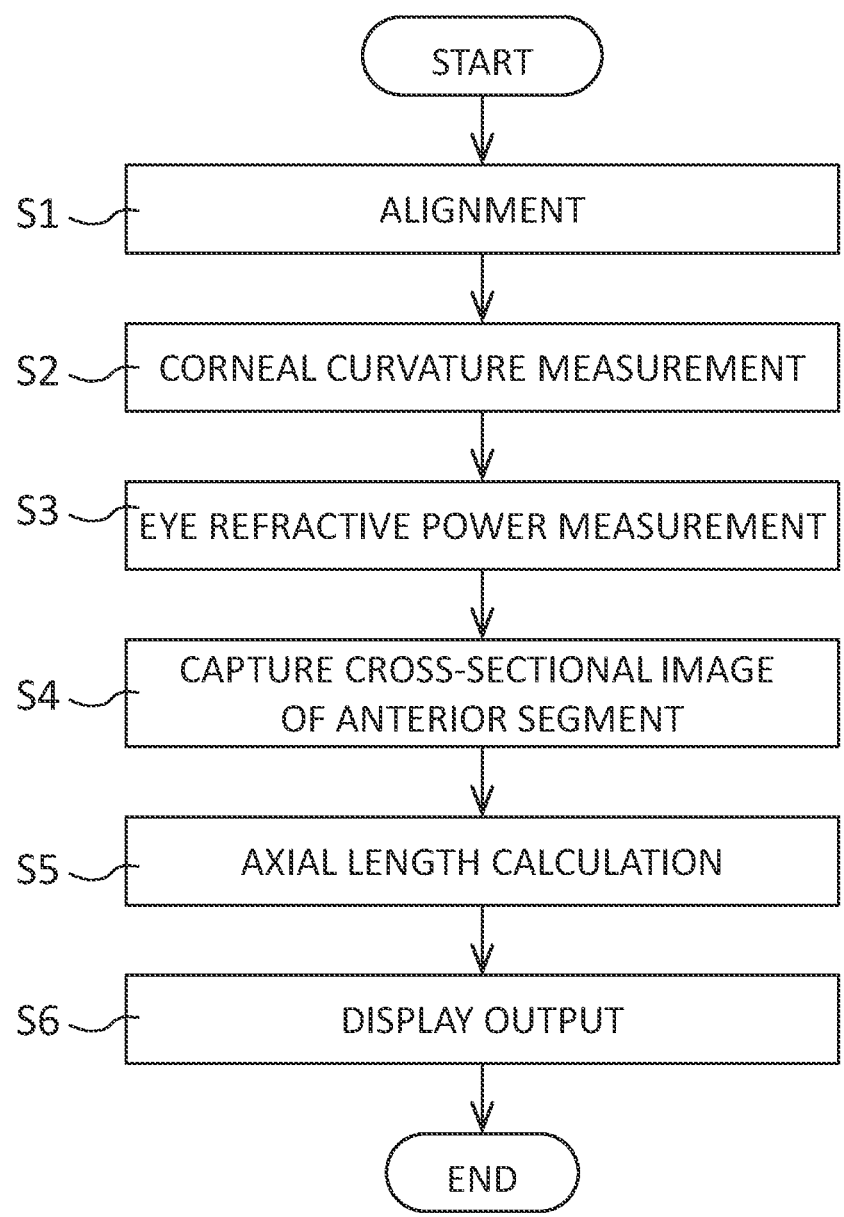

OPHTHALMIC APPARATUS

CROSS-REFERENCE TO RELATED APPLICATION

This application claims priority from Japanese Patent Applications No. 2020-060070, No. 2020-060071 and No. 2020-060072 filed on Mar. 30, 2020, the entire subject-matter of which is incorporated herein by reference.

TECHNICAL FIELD

The present disclosure relates to an ophthalmic apparatus for acquiring an axial length of a subject eye.

BACKGROUND

Ultrasonic type and optical interference type axial length measurement apparatuses are used in prescriptions of intraocular lenses.

The ultrasonic type axial length measurement apparatus is a contact type, and the measurement is performed by bringing a probe into contact with a cornea.

In the optical interference type axial length measurement apparatus, two methods including a TD method (a time domain method) and an SS method (a swept source method) are mainstreams. A coherent light source is used in the TD method, whereas a wavelength sweep light source is used in the SS method (refer to JP-A-2012-224621 and JP-A-2019-063044).

In recent years, a prevalence of myopia, especially among young people, has been remarkably increasing regardless of the country. As myopia progresses with the extension of an axial length, the risk of blindness increases, which is becoming a major social problem. Against such a background, evaluation of the myopia progression based on the axial length is drawing an attention. In order for the young people to be appropriately examined, it is desired that the axial length measurement apparatus be widely used not only in cataract treatment facilities but also in more facilities (hospital facilities, school facilities, and the like).

However, since the ultrasonic axial length measurement apparatus is the contact type, examiners are limited and the burden on the examinee is large. In addition, the optical interference type axial length measurement apparatus is expensive in terms of apparatus configuration such as a light source. Therefore, the price of the apparatus can hinder the spread to the facilities.

SUMMARY

The inventor of the present application examined a new method for measuring the axial length and an apparatus configuration for realizing the new method.

An object of the present disclosure is to provide a novel ophthalmic apparatus by any one of the method for measuring the axial length and the apparatus configuration.

An ophthalmic apparatus according to a first aspect of the present disclosure, includes:
- a first optical system that irradiates a fundus of a subject eye with measurement light, the first optical system for acquiring information regarding an eye refractive power of the subject eye based on reflection light of the measurement light reflected from the fundus;
- a second optical system for acquiring anterior segment information regarding a shape of an anterior segment, the anterior segment information being related to a cross section on which an optical axis of the first optical system is arranged; and
- a calculation controller,
- in which the calculation controller acquires an axial length of the subject eye based on an on-surface eye refractive power, which is the eye refractive power on the cross section, and the anterior segment information related to the cross section.

BRIEF DESCRIPTION OF DRAWINGS

FIG. 7 is a diagram illustrating a refractivity in each meridian direction when SPH=−SD, CYL=−2D, and AXIS=30°.

DETAILED DESCRIPTION

[Overview]

Figure 1:
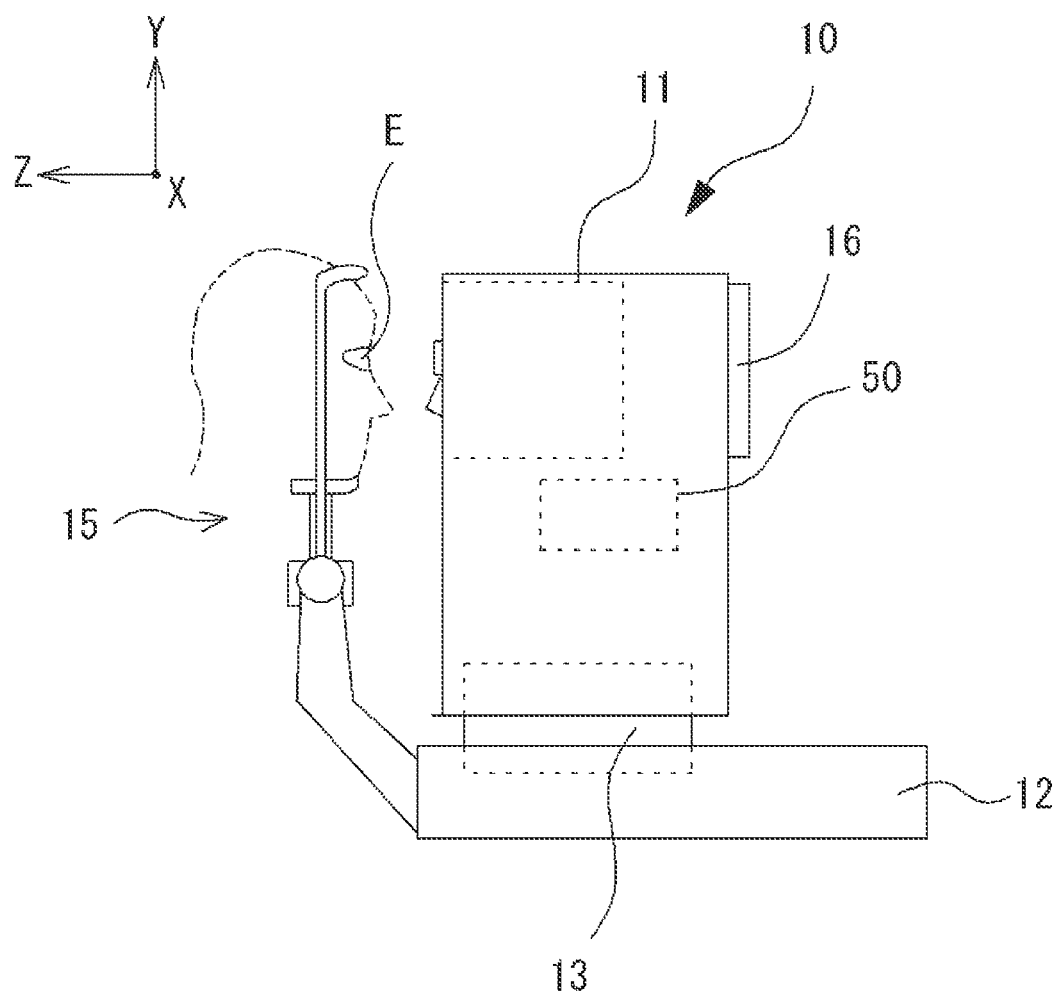
FIG. 1 is an external view illustrating a schematic configuration of an ophthalmic apparatus according to an application example.

Embodiments of the present disclosure will be described. Items classified by "<" and ">" hereinafter can be used independently or in relation to each other. For example, in a certain embodiment, a plurality of items can be appropriately combined. In addition, for example, the items described for one embodiment can be applied to other embodiments.

First Embodiment

First, an ophthalmic apparatus and an axial length calculation program according to the first embodiment will be described. In the first embodiment, an ophthalmic apparatus and an axial length calculation program acquires an axial length of a subject eye based on information regarding an eye refractive power of the subject eye acquired via a first optical system and anterior segment information acquired via a second optical system.

<Apparatus Configuration>

The ophthalmic apparatus according to the first embodiment includes at least a first optical system, a second optical system, and a calculation controller. The ophthalmic apparatus may additionally include a fixation target display optical system.

The axial length calculation program is executed by the calculation controller. For convenience, unless otherwise noted, in the following embodiments, it is assumed that the axial length calculation program is executed by the ophthalmic apparatus (an example of an ophthalmic computer).

<First Optical System>

The first optical system is used for acquiring the information regarding the eye refractive power of the subject eye. The first optical system projects measurement light to a fundus of the subject eye. The information regarding the eye refractive power is acquired based on reflection light of the measurement light reflected from the fundus. The first optical system may be, for example, a measurement optical system of an objective type eye refractive power measurement apparatus such as an auto refractometer and a wave front sensor.

In the present embodiment, the measurement light from the first optical system is assumed to be infrared light. However, the present disclosure is not limited to this, and visible light may be used.

<Second Optical System>

The second optical system is used for acquiring anterior segment information, which is information about the shape of the anterior segment.

In the first embodiment, the anterior segment information about a cross section may be acquired via the second optical system. In this case, an optical axis of the first optical system is arranged on the surface of the cross section.

The second optical system may be a cross-sectional imaging optical system such as a Scheimpflug optical system, or may be another optical system. When the Scheimpflug optical system is used as the second optical system, it is required that a light projection axis of the illumination light in the second optical system and a light projection axis of the measurement light in the first optical system are arranged on the identical axis.

<Example of Anterior Segment Information>

The anterior segment information may include information on the shape of an ocular media in the anterior segment. The anterior segment information may be an image of the anterior segment. From the anterior segment information, the shape of the ocular media in the anterior segment can be specified. For example, it is desirable that two or more of a corneal thickness, an corneal front surface curvature radius, a corneal rear surface curvature radius, an anterior chamber depth, a crystalline lens thickness, an crystalline lens front surface curvature radius, and a crystalline lens rear surface curvature radius can be specified based on the anterior segment information. Of course, these values that specify the shape of the ocular media may be the anterior segment information.

The anterior segment information acquired via the second optical system may include at least the information on the shape of the crystalline lens. In addition, a shape of a measurement region by the first optical system may be specified by the anterior segment information acquired via the second optical system. The measurement region is a region where the eye refractive power is measured by the first optical system.

<Fixation Target Display Optical System>

The ophthalmic apparatus may include a fixation target display optical system. The fixation target display optical system is an optical system that displays a fixation target with respect to the subject eye, and may be used in each operation of the first optical system and the second optical system.

The fixation target display optical system in the present embodiment may be capable of changing a fixation target display distance. Such fixation target display optical system may be used to perform fogging on the subject eye when measuring the refractive power by the first optical system. The first optical system may also be used for an intraocular accommodation of the subject eye.

<Method of Deriving Axial Length (Axial Length Calculation Program)>

In the first embodiment, the calculation controller acquires the axial length of the subject eye based on the eye refractive power and the anterior segment information.

The eye refractive power and the anterior segment information may be acquired based on measuring or imaging. In addition, what is measured or imaged by another device may be acquired by being stored in a memory.

In this case, the axial length may be acquired based on an on-surface eye refractive power which is the eye refractive power on the cross section, and the anterior segment information on the cross section. Since the eye refractive power and the information for specifying the shape of the anterior segment is the information about the same cross section, the axial length can be easily and appropriately derived. In this case, since the information that specifies the shape of the measurement region by the first optical system is used as the anterior segment information relating to the cross section, the axial length can be appropriately obtained.

Here, for example, the calculation controller may derive the axial length by ray tracing techniques. In the ray tracing techniques, a position of the far point may be specified based on the on-surface eye refractive power.

In the ray tracing techniques, a distance between an intersection point when a light beam incident on a predetermined position in the anterior segment from the far point intersects the optical axis after being refracted by the ocular media, and a corneal apex, is derived as the axial length. In this case, instead of the equivalent spherical power generally used when specifying the far point in the field of ophthalmology, the eye refractive power on the cross section (on-surface refractive power) may be used. In this way, the position of the far point of the light beam passing over the cross section is more appropriately specified. As a result, the axial length can be obtained more appropriately. In this case, the ray tracing techniques may be performed for each of the plurality of light beams, and the axial length may be obtained as a result of the ray tracing techniques of each light beam. For example, an average value (may be a weighted average) of the axial lengths obtained by each ray tracing may be obtained as the axial length of the subject eye.

In the ray tracing techniques, the incident position of the light beam with respect to a boundary surface of each ocular media and a change in the angle at the boundary surface are determined by taking the shape of the ocular media on the cross section specified from the anterior segment information into consideration. More detailed description of the light beam tracing method will be described in the application examples described later.

In addition, when deriving the axial length from the eye refractive power and the anterior segment information for the same cross section, the calculation controller may take an eccentricity of the ocular media of the anterior segment into consideration. The eccentricity is specified based on the anterior segment information. As a result of considering the eccentricity of the ocular media within the cross section, the axial length can be obtained more appropriately. In this case, for example, the ray tracing techniques may be performed on each of a plurality of light beams including at least a first light beam and a second light beam, and then, the axial length may be obtained for each light beam, and the final measurement value may be obtained based on the plurality of axial lengths. The first light beam and the second light beam are light beams arranged across the eye axis on the cross section.

<Specific Example of Second Optical System: Cross-Sectional Imaging Optical System>

In the first embodiment, the second optical system may be a cross-sectional imaging optical system that captures a cross-sectional image of the cross section set in the anterior segment of the subject eye. The cross-sectional imaging optical system may be, for example, a Scheimpflug optical system or may be an OCT optical system. From the cross-sectional image, it is possible to specify not only the shape of the boundary surface (surface) in each ocular media but also the distance between the boundary surfaces. As a result, the axial length can be obtained more accurately. When the second optical system is a cross-sectional imaging optical system, it is preferable that an area from the front surface of the cornea of the subject eye to at least the front surface of the crystalline lens is included in the imaging area of the cross-sectional imaging optical system. Needless to say, it is also preferable an area from the front surface of the cornea to the rear surface of the crystalline lens is included in the imaging area. Since the corneal thickness, the corneal front surface curvature radius, the corneal rear surface curvature radius, the anterior chamber depth, the crystalline lens thickness, the crystalline lens front surface curvature radius, and the crystalline lens rear surface curvature radius can be acquired without omission, the axial length can be appropriately acquired.

When the second optical system is a Scheimpflug optical system, the light projection axis of the illumination light needs to be arranged on the identical axis with the light projection axis of the measurement light in the first optical system. In addition, the projection optical system of the Scheimpflug optical system may emit the slit light as the illumination light. The emission area of the slit light is set as the cross section. In addition, a light receiving optical system of the Scheimpflug optical system has a lens system and an image sensor element arranged in a relationship of the cross section and the Scheimpflug. In the light receiving optical system, a light receiving optical axis inclined with respect to the cross section is arranged.

Visible light may be emitted or infrared light may be emitted as the slit light. Visible light is more likely to be scattered in the ocular media than infrared light. On the other hand, when the infrared light is emitted, the burden on the examine at the time of imaging can be suppressed.

In addition, when the second optical system is an OCT optical system, not only the anterior segment OCT but also the fundus OCT may be imaged. In this case, it is not necessary that the anterior segment OCT and the fundus OCT can be imaged once, but by switching a part of the OCT optical system, the anterior segment OCT and the fundus OCT may be imaged individually.

<Specific Example of Second Optical System: Purkinje Image Acquisition Optical System>

Instead of the cross-sectional imaging optical system, a Purkinje image acquisition optical system may be applied as the second optical system. The Purkinje image acquisition optical system includes an index projector that projects a measurement index (referred to as a pattern index) having a certain pattern onto the anterior segment from the front face facing the subject eye, and a front imaging optical system that captures the Purkinje image using the pattern index. In this case, a first Purkinje image (reflection image by the front surface of the cornea), a second Purkinje image (reflection image by the rear surface of the cornea), a third Purkinje image (reflection image by the front surface of the crystalline lens), and a fourth Purkinje image (reflection image by the rear surface of the crystalline lens) can be generated respectively. It is conceivable that the shape of the boundary surface corresponding to each Purkinje image can be obtained based on the position information of each Purkinje image. However, the corneal thickness, the anterior chamber depth, the crystalline lens thickness, and the like cannot be acquired only from the position information of the Purkinje image. That is, the distance between the boundary surfaces of the ocular media cannot be acquired. On the other hand, the cross-sectional imaging optical system is more advantageous in acquiring the distance between the boundary surfaces. In addition, since the third Purkinje image (reflection image by the front surface of the crystalline lens) is generated near the optical axis of the front imaging optical system as compared with the first, the second, and the fourth Purkinje images, the difference in the shape of the front surface of the crystalline lens is unlikely to appear as the difference in the appearance position of the third Purkinje image. Therefore, if the cross-sectional imaging optical system in which the area from the front surface of the cornea to at least the front surface of the crystalline lens of the subject eye is included in the imaging area, the information on the shape of the front surface of the crystalline lens can be accurately acquired, which is more advantageous than the Purkinje image acquisition optical system.

The pattern index projected from the index projector may be a ring-shaped pattern, or may be another two-dimensional pattern formed by lines or a plurality of points. For example, a plurality of point indices arranged on the circumference may be projected as a pattern index. In addition, a combinations of a plurality of patterns may be a pattern index.

<Measurement Control>

In order to appropriately obtain the axial length using the method described above, it is desirable that the information on the shape of the more types of the translucent bodies is included in the anterior segment information. In this case, it is conceivable that at least the information on the shape of the crystalline lens is included in the anterior segment information. In this case, the eye refractive power measured by the first optical system and the information on the shape of the crystalline lens included in the anterior segment information are inevitably affected by the intraocular accommodation. Therefore, in order to ensure the accuracy and reproducibility of the axial length, it is required to acquire the information regarding the eye refractive power and the anterior segment information, respectively, while considering the state of intraocular accommodation.

On the other hand, in the present embodiment, the calculation controller may control the first optical system and the second optical system so that each of the information regarding the eye refractive power and the anterior segment information are acquired in a state where the intraocular accommodations are identical.

If each of the information regarding the eye refractive power and the anterior segment information are acquired in a state where the intraocular accommodations are identical each other, since each of the acquired information is equally affected by the accommodation, the axial length can be appropriately obtained.

In this case, the calculation controller may control the acquisition timing of each of the eye refractive power and the anterior segment information such that the accommodation given to the subject eye by the fixation target become the same between the acquisition time of the eye refractive power and the acquisition time of the anterior segment information. The acquisition timing may be controlled in conjunction with the change control of the fixation target display distance.

The acquisition timing may be controlled such that the display positions of the fixation targets are identical each other between the acquisition time of the eye refractive power and the acquisition time of the anterior segment information.

In addition, for example, the calculation controller may synchronize the acquisition timings of each of the eye refractive power and the anterior segment information. The term "synchronization" here does not necessarily mean that the acquisition timings are completely the same. For example, there may be a time difference between the acquisition timings in a degree of no significant difference in the accommodation state.

In addition, the calculation controller may add the fogging to the subject eye by controlling the fixation target display optical system, and may acquire each of the information regarding the eye refractive power and the anterior segment information when the subject eye is in the unaccommodated state. The accuracy and the reproducibility of the axial length is further improved when obtaining the axial length based on the eye refractive power and the anterior segment information acquired in the unaccommodated state compared to a case where the axial length is obtained from the eye refractive power and the anterior segment information measured in the accommodated state.

Incidentally, as described above, the second optical system used for acquiring the anterior segment information may be a Scheimpflug optical system, and in this case, it is assumed that the anterior segment is irradiated with the visible as the illumination light, and the cross-sectional image of the anterior segment is captured. On the other hand, the infrared light is used as the measurement light for the measurement of eye refractive power.

When the cross-sectional image is captured in the Scheimpflug optical system, relatively strong visible light is emitted as the projection light. In this case, the strong visible light emission may surprise the examinee, and as a result, the alignment state may be changed. On the other hand, the calculation controller may perform the acquisition operation for the eye refractive power, and then, may perform the operation for acquiring the anterior segment information at the timing when the acquisition operation is completed. In this way, the alignment deviation is suppressed between the acquisition time of the eye refractive power and the acquisition time of the cross-sectional image which is the anterior segment information. In addition, in this case, an order of performing each operation may be an order of fogging→acquisition of the eye refractive power→acquisition of the anterior segment information. In addition, as described above, since the completion timing of operation for acquiring the information regarding the eye refractive power and the timing of performing the operation for performing the anterior segment information are substantially identical, it is unlikely to occur the deviation between the acquisition time of the eye refractive power and the acquisition time of the cross-sectional image, which is the anterior segment information, for each of the accommodation and alignment states. As a result, the accuracy and the reproducibility of the axial length is improved.

As described above, in the ophthalmic apparatus in the first embodiment, the axial length is measured by a new method and a new apparatus configuration different from the axial length measurement apparatus in the related art.

Here, the first optical system can acquire the information regarding the eye refractive power of the subject eye, which is important in the evaluation of myopia. The ophthalmic apparatus in the first embodiment can acquire the important information in the evaluation of the myopia, such as the eye refractive power and the axial length, using one unit.

In particular, in the first embodiment, when the Scheimpflug optical system is used as the second optical system, while sufficiently suppressing apparatus cost compared to that of the optical interference type axial length measurement apparatus, it is easy to satisfy the axial length measurement accuracy required for monitoring the myopia progression.

<Acquisition of Axial Length from Plurality of Cross Sections>

In the description described above, the axial length is obtained using the anterior segment information for one cross section. However, the present disclosure is not limited thereto, and a plurality of anterior segment information may be acquired for each of the plurality of cross sections. In this case, the axial length may be derived by using the above-described method for each cross section. For example, an average value of the axial lengths obtained for each cross section may be obtained.

In the Scheimpflug optical system, as a method for imaging a plurality of cross sections, a method in which a light receiving optical system is rotated around a light projection axis is known, and this method may be used.

Second Embodiment

Next, the second embodiment will be described.

The ophthalmic according to the second embodiment further includes a third optical system in addition to the apparatus configuration in the first embodiment. That is, the ophthalmic apparatus according to the second embodiment includes a first optical system, a second optical system, a third optical system, and a calculation controller.

Regarding the configuration common to that of the first embodiment, the description of the first embodiment will be appropriately incorporated, and the details will be omitted. However, in the second embodiment, the second optical system is described as being an anterior segment cross-sectional imaging optical system and being a Scheimpflug optical system unless otherwise specified.

In the second embodiment, the third optical system includes an index projector that projects a pattern index for measuring the corneal shape onto the anterior segment from the front face facing the subject eye. The third optical system may additionally include a front imaging optical system that captures a corneal Purkinje image using the pattern index. The corneal Purkinje image may be captured as the anterior segment front image.

In the second embodiment, the calculation controller may acquire the axial length based on the eye refractive power and the anterior segment information relating to the cross section and corneal shape information based on the corneal Purkinje image.

Here, the corneal shape information including at least the curvature radius of the front surface of the cornea can be obtained with higher accuracy by deriving from the corneal Purkinje image than by obtaining from the anterior segment cross-sectional image captured by the Scheimpflug optical system. Therefore, for example, in the axial length calculation, a part of information about the cornea in the anterior segment information may be replaced by the corneal shape information derived from the corneal Purkinje image. In addition, a part or all of the anterior segment information may be corrected based on the corneal shape information. As a specific example of the correction, after deforming the entire anterior segment cross-sectional image such that the corneal shape of the anterior segment cross-sectional image matches the corneal shape based on the corneal Purkinje image, the shape of each ocular media based on the deformed image may be used for the axial length calculation.

As described above, in the axial length calculation, the axial length can be obtained more appropriately by taking the corneal shape information derived from the corneal Purkinje image into consideration.

In the second optical system which is the Scheimpflug optical system, it becomes easier to expand the imaging area in the depth direction as the inclination of the optical axis with respect to the cross section (object surface) decreases. In other words, the smaller the inclination of the light receiving optical axis (imaging optical axis) of the second optical system with respect to the cross section (object surface), the more advantageous it is for the second optical system to image the area from the front surface of the cornea to the rear surface of the crystalline lens using. However, when the light receiving optical axis is inclined to the extent that the area from the front surface of the cornea to the rear surface of the crystalline lens can be imaged, there is a risk that the light receiving optical system in the optical system of the second optical system and the index projector in the third optical system will interfere spatially.

This will be described in more detail. Usually, in a kerato measurement which is one of the methods for measuring corneal shape, one or more circumferential regions within a range of φ2 mm to φ4 mm of the cornea are often used as the measurement region. In this case, the light flux forming the pattern index is projected at an angle in a range of 14° (corresponding to φ2 mm) to 29° (corresponding to φ4 mm) with respect to the eye axis.

On the other hand, when trying to image the area from the front surface of the cornea to the rear surface of the crystalline lens with the Scheimpflug optical system which is the second optical system, it is desirable that the angle between the light receiving optical axis of the second optical system and the cross section become smaller. The ophthalmic Scheimpflug cameras in the related art are mainly used in anterior segment analyzers, and since the low distortion and high resolution are prioritized, the above-described angle is approximately 45° or larger. On the other hand, the above-described angle in the Scheimpflug optical system in the present embodiment is approximately 40° or less, giving priority to being able to image deeper area. Therefore, each light flux emission position in the index projector and the light receiving optical axis of the second optical system can be arranged on substantially the same circumference with respect to a visual axis. In addition, considering the size of the optical element of each unit, the above-described interference problem may occur.

On the other hand, in the second embodiment, the index projector of the third optical system is arranged so as to avoid the light receiving optical axis in the second optical system. More specifically, the index projector of the third optical system may be arranged so as to avoid the normal direction (at least the direction in which the light receiving optical system of the second optical system is placed) of the cross section of the anterior segment formed by the second optical system. For example, if the normal direction is the vertical direction, the index projector of the third optical system may be arranged so as to avoid a position that is a direction of +90° with respect to the optical axis of the third optical system (the horizontal direction is) 0°.

The pattern index projected from the index projector is formed avoiding the position that is the direction of +90° (the horizontal direction is) 0° with respect to the optical axis of the third optical system. The pattern index may have a pattern shape that is symmetrical with respect to the optical axis of the third optical system. For example, the pattern may be a line or a two-dimensional pattern formed by a plurality of points. For example, a plurality of point indices arranged on the circumference may be projected as a pattern index. In addition, a combinations of a plurality of patterns may be a pattern index.

[Application Example]

Next, one application example corresponding to the first and second embodiments will be described with reference to FIGS. 1 to 7.

<Overall Configuration of Application Example>

First, a schematic configuration of an ophthalmic apparatus 10 according to an application example will be described with reference to FIG. 1.

In this application example, the ophthalmic apparatus 10 is a multifunction apparatus of an objective eye refractive power measurement apparatus (particularly, in the present application example, an auto-refractometer) and a Scheimpflug camera. In the present application example, the ophthalmic apparatus 10 is a stationary type examination apparatus, but the present disclosure is not limited thereto, and a handheld type may be used.

As illustrated in FIG. 1, the ophthalmic apparatus 10 includes at least a measurement unit 11, a base 12, an alignment drive unit 13, a face support unit 15, a monitor 16, and a calculation controller 50.

Figure 2:
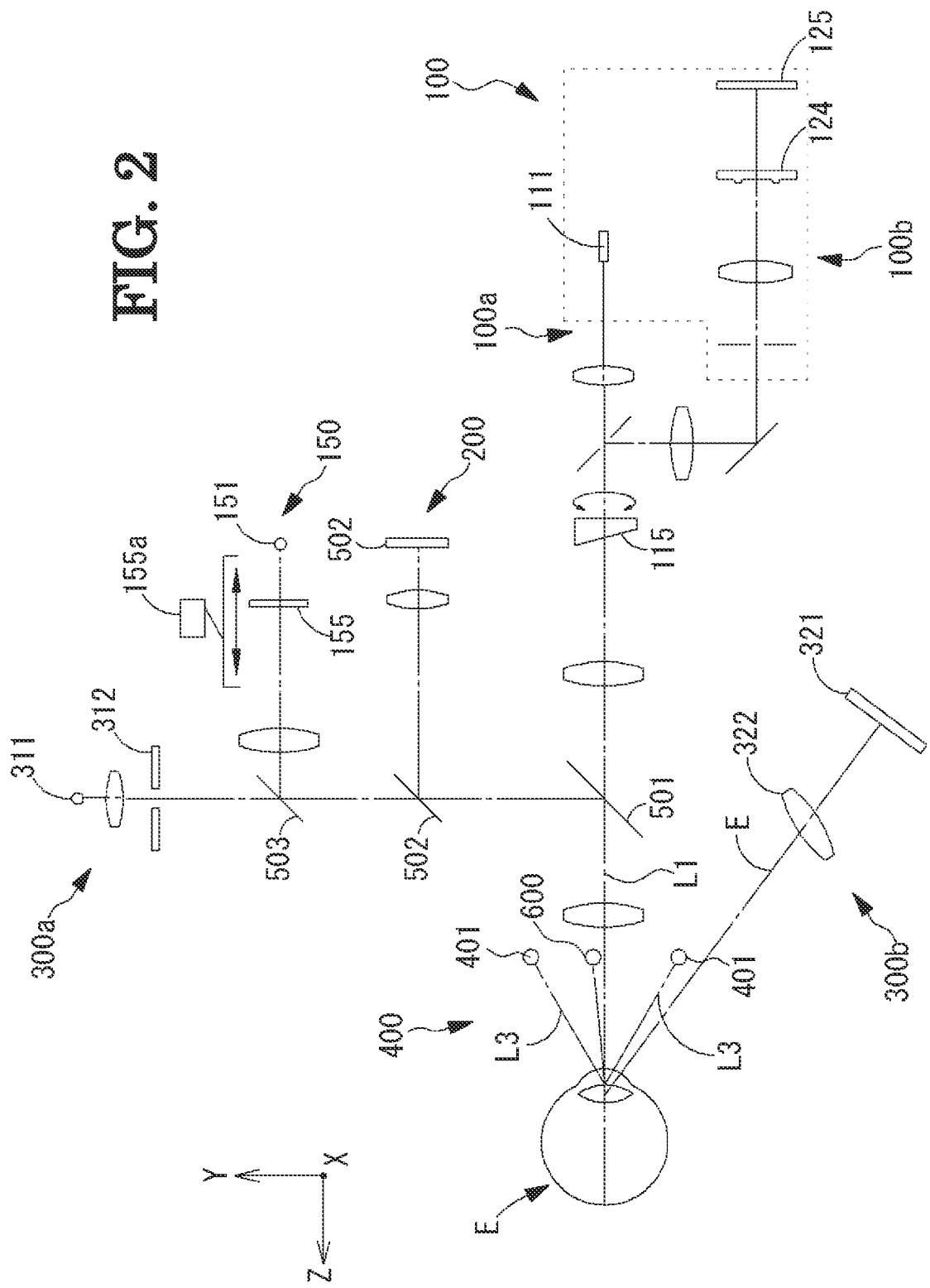
FIG. 2 is a schematic configuration diagram of an optical system in the ophthalmic apparatus.
Figure 3:
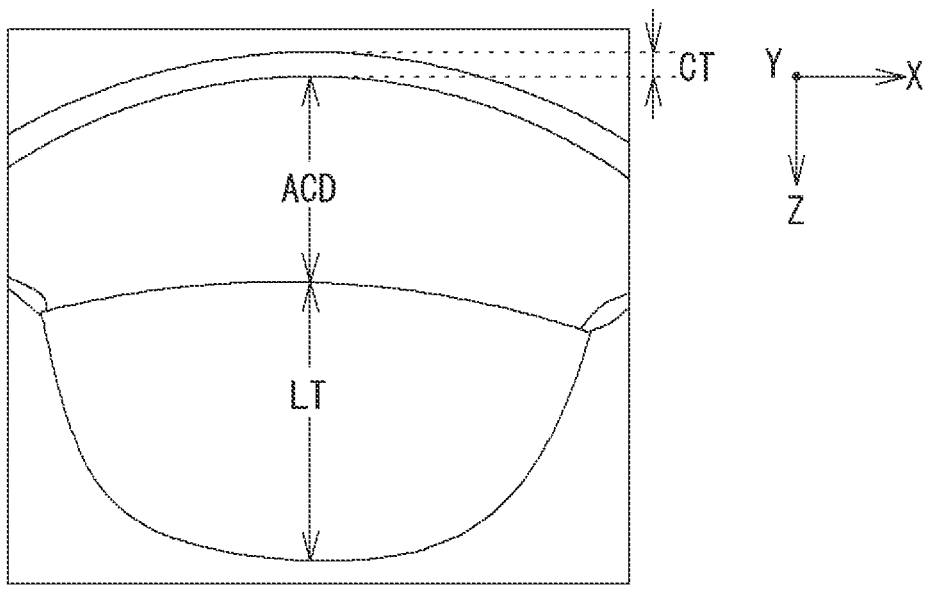
FIG. 3 is a diagram illustrating an anterior segment cross-sectional image captured by a cross-sectional imaging optical system.

The measurement unit 11 includes a measurement system, an imaging system, and the like that are used for examining the subject eye. In the present application example, the optical system illustrated in FIG. 2 is arranged.

The alignment drive unit 13 may be able to three-dimensionally move the measurement unit 11 with respect to the base 12.

The face support unit 102 is used to fix the examinee's face in front of the measurement unit 11. The face support unit 102 is fixed to the base 12 and supports the examinee's face.

The calculation controller (also called as a processor, hereinafter, simply referred to as a controller) 50 performs overall control of the entire ophthalmic apparatus 10. It also performs processing on various examine results acquired via the measurement unit 11.

<Optical System>

Next, the optical system in the ophthalmic apparatus 10 will be described with reference to FIG. 2.

As an example, the ophthalmic apparatus 10 includes a measurement optical system 100, a fixation target display optical system 150, a front imaging optical system 200, cross-sectional imaging optical systems 300a and 300b, and an index projection optical system 400. In addition, beep splitters 501, 502, and 503 that branch and combine the optical paths of each optical system.

<Measurement Optical System>

The measurement optical system 100 objectively measures the eye refractive power of the subject eye E. For example, each value of spherical power (SPH), columnar power (CYL), and astigmatism axis angle (AXIS) may be acquired as the measurement results of eye refractive power.

The measurement optical system 100 includes a projection optical system 100a and a light receiving optical system 100b.

The projection optical system 100a includes at least a measurement light source 111, and projects a spot-shaped measurement light onto the fundus of the subject eye E via the central portion or the corneal apex of the pupil P in the subject eye E. In the present application example, infrared light is used as the measurement light. However, the measurement light is not necessarily limited to this, and the measurement light may be visible light. The measurement light source 111 may be an SLD light source, an LED light source, or another light source.

In the present application example, a prism 115 is arranged on the common path of the projection optical system 100a and the light receiving optical system 100b. By rotating the prism 115 around the optical axis L1, the projected light flux on the pupil is eccentrically rotated at a high speed. As an example, in the present application example, the projected light flux is eccentrically rotated in the region of φ2 mm to φ4 mm on the pupil. This region is the measurement region of eye refractive power in the present application example.

The light receiving optical system 100b includes at least a ring lens 124 and an image sensor element 125. As illustrated in FIG. 2, the measurement optical system 100 may also include optical elements such as a lens and an aperture. The light receiving optical system 100b takes out the reflection light flux of the measurement light flux reflected from the fundus in a ring shape via the peripheral portion of the pupil. The ring lens 124 is positioned at the pupil conjugate position and the image sensor element 125 is positioned at the fundus conjugate position. The eye refractive power is derived by analyzing the ring image formed on the image sensor element 125 via the ring lens 124.

As described above, in the present application example, the measurement light is eccentrically rotated on the pupil at a high speed, the analysis processing is performed on the output image from the image sensor element 125 based on the exposure for a sufficiently long time compared to the rotation period, or the added image of the image data sequentially output from the image sensor element 125, and then, the eye refractive power is derived. In the present application example, the values of the spherical power (SPH), columnar power (CYL), and astigmatism axis angle (AXIS) are acquired as the measurement results of analysis processing.

<Fixation Target Display Optical System>

The fixation target display optical system 300 displays a fixation target to the subject eye E. The fixation target is displayed on the optical axis of the measurement optical system 100. The fixation target display optical system 300 is used for fixing the subject eye. It is also used to apply fogging and regulatory loads to the subject eye. For example, the fixation target display optical system 300 includes at least a light source 151 and a fixation target plate 155. The fixation target plate 155 can be moved along the optical axis by the drive unit 155a. As a result, the fixation target display distance (display position) for the subject eye E can be changed.

<Front Imaging Optical System>

The front imaging optical system 200 captures a front image of the anterior segment of the subject eye E. For example, the front imaging optical system 200 includes an image sensor element 205 and the like. As the front image, an observation image of the anterior segment may be acquired. The observation image is used for the alignment and the like. In addition, an index image (pattern index image) by the pattern index projected onto the cornea of the subject eye from the index projection optical system 400 is imaged by the front imaging optical system 200.

<Cross-Sectional Imaging Optical System>

The cross-sectional imaging optical systems 300a and 300b are used for capturing the cross-sectional image of the anterior segment. The cross-sectional imaging optical systems 300a and 300b include an emission optical system 300a and a light receiving optical system 300b. The emission optical system 300a irradiates the anterior segment with the slit light on the identical axis with the light projection axis (optical axis L1) of the measurement light of the measurement optical system 100. The emission optical system 300a includes a light source 311, a slit 312, and the like. In the present application example, the slit light, which is the illumination light, is visible light. For example, a visible light source that emits blue light may be used as the light source 311.

In the present application example, a cross-section through which the slit light passes in the anterior segment is referred to as the "cross section". The cross section is an object surface of the cross-sectional imaging optical systems 300a and 300b. In FIG. 2, the horizontal direction (the depth direction of the paper in FIG. 2) of the opening of the slit 312 is the longitudinal direction. Therefore, in the present application example, the horizontal plane (XZ cross section) including the optical axis L1 is set as the cross section. In the present application example, the cross section is formed at least between the front surface of the cornea and the rear surface of the crystalline lens.

The light receiving optical system 300b includes a lens system 322, an image sensor element 321 and the like. In the light receiving optical system 300, the lens system 322 and the image sensor element 321 are arranged in a Scheimpflug relationship with the cross section set in the anterior segment. That is, the optical arrangement is such that each of the extension surfaces of the cross section, the main plane of the lens system 322, and the imaging surface of the image sensor element 321 intersect each other at one line of intersection (one axis). The cross-sectional image of the anterior segment (refer to FIG. 3) is acquired based on the signal from the image sensor element 321.

<Index Projection Optical System>

Figure 4A:
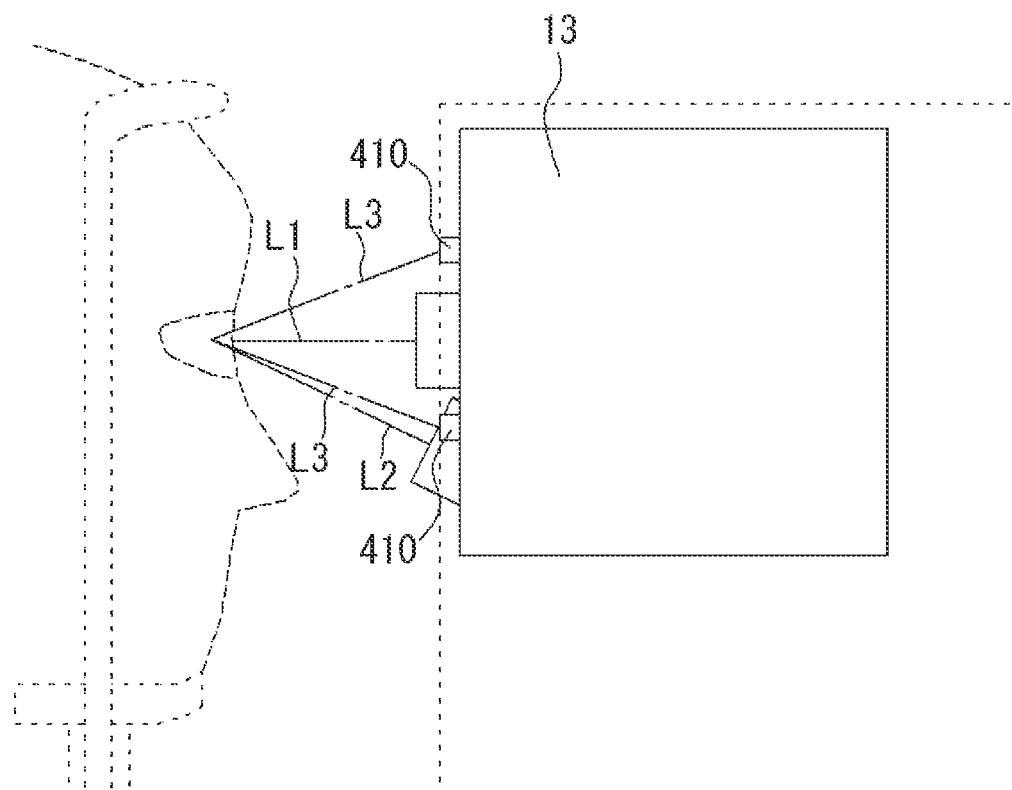
FIG. 4A is a side view of the measurement unit, and is a diagram illustrating a positional relationship between an index projector and an optical axis of the cross-sectional imaging optical system.
Figure 4B:
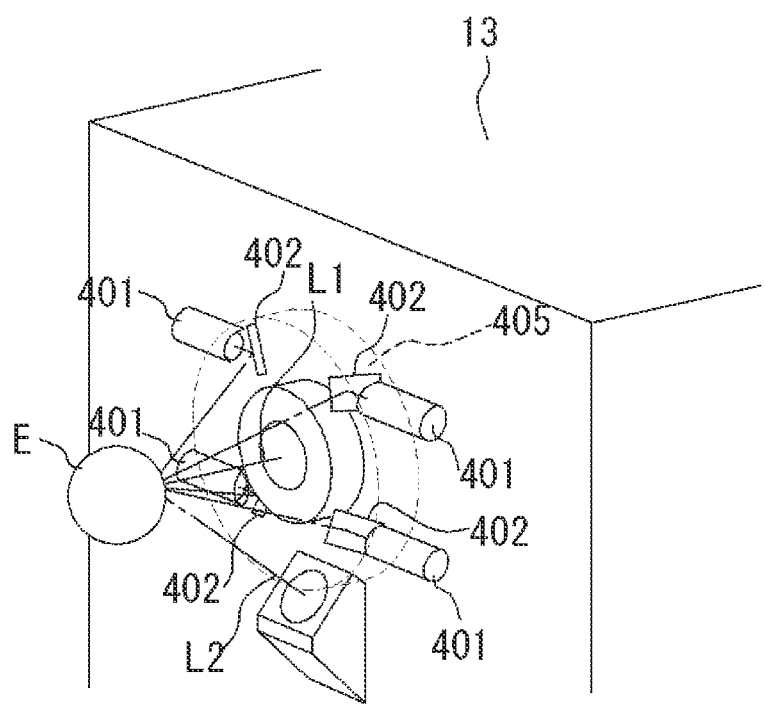
FIG. 4B is a perspective view of the measurement unit, and is a diagram illustrating the positional relationship between the index projector and the optical axis of the cross-sectional imaging optical system.

In the present application example, the index projection optical system 400 includes a plurality of point light sources 401. In the present application example, each point light source 401 emits infrared light. However, it may be visible light. As illustrated in FIGS. 4A and 4B, in the present application example, the index projection optical system 400 is arranged in front of the measurement unit 11 as the index projector 410. The index projection optical system 400 projects a pattern index for measuring the corneal shape onto the anterior segment from the front face facing the subject eye. In the present application example, a pattern index by the point image of four-points symmetrical to the optical axis L1 is projected onto the cornea. The circumferential region on which the pattern index is projected is the measurement region of the corneal shape by the index projection optical system 400 and the front imaging optical system 200. As an example, in the present application example, when a cornea model eye having a predetermined curvature radius is positioned at a predetermined working distance, each point image configuring the pattern index is projected onto the φ3 mm of the circumferential region of the cornea model eye. In the present application example, the pattern index is configured with point image of four points, but the number of indices is not necessarily limited thereto. The pattern index may be configured with the plural point image of three or more points, or may include a linear index image or the like.

By the way, in the present application example, the light receiving optical axis L2 in the cross-sectional imaging optical system 300 is arranged directly below the optical axis L1 (in the direction of −90°). In order to realize an imaging area from the front surface of the cornea to the rear surface of the crystalline lens, as a result of the fact that the inclination of the light receiving optical axis of the second optical system with respect to the cross section is sufficiently small, when the apparatus is viewed from the side, the light beam of the pattern index projected from the index projection optical system 400 and the light receiving optical axis L2 are placed in a close positional relationship (refer to FIG. 4A).

Here, in FIG. 4B, the index projector 450 that is virtually arranged (not actually arranged) in the measurement unit 13 is illustrated by a dashed line. The index projector 450 projects the Mayer ring on the same circumferential region as the index projector 400. If the light beam of the pattern index and the light receiving optical axis L2 have a close positional relationship, when trying to project a pattern index on a ring such as the Mayer ring, it can be seen that the light receiving optical axis L2 interferes with the index projector 450.

On the other hand, the index projector 410 is arranged so as to avoid the lower part of the optical axis L1. For example, in FIG. 4B, an example of an apparatus configuration is illustrated, in which the light source 401 and a mirror 402 (not illustrated in FIG. 2) for angle adjustment are arranged at four locations of the upper right, lower right, upper left, and lower left part of the optical axis L1. In the present application example, a pattern index based on the four-point image symmetrical with respect to optical axis L1 is projected onto the cornea. In the present application example, as a result of such an arrangement of the index projector 410, both wide-area imaging by the cross-sectional imaging optical system 300 and the acquisition of the corneal shape by the Purkinje image are realized.

<Alignment Index Projection Optical System>

Furthermore, the ophthalmic apparatus 10 includes a light source 600 for alignment. Two light sources 600 for alignment may be provided on each side of left and right. For example, a light flux is projected along a horizontal plane that includes the optical axis L1. In the present application example, the alignment index projection optical system is formed by the index projection optical system 400 and the light source 600. Diffused light is projected from one of the index projection optical system 400 and the light source 600, and parallel light is projected from the other. The working distance may be adjusted by moving the corneal Purkinje image due to the parallel light and the Purkinje image due to the diffused light them in the front-rear direction such that those images are captured in a predetermined ratio.

<Control Operation>

Figure 5:
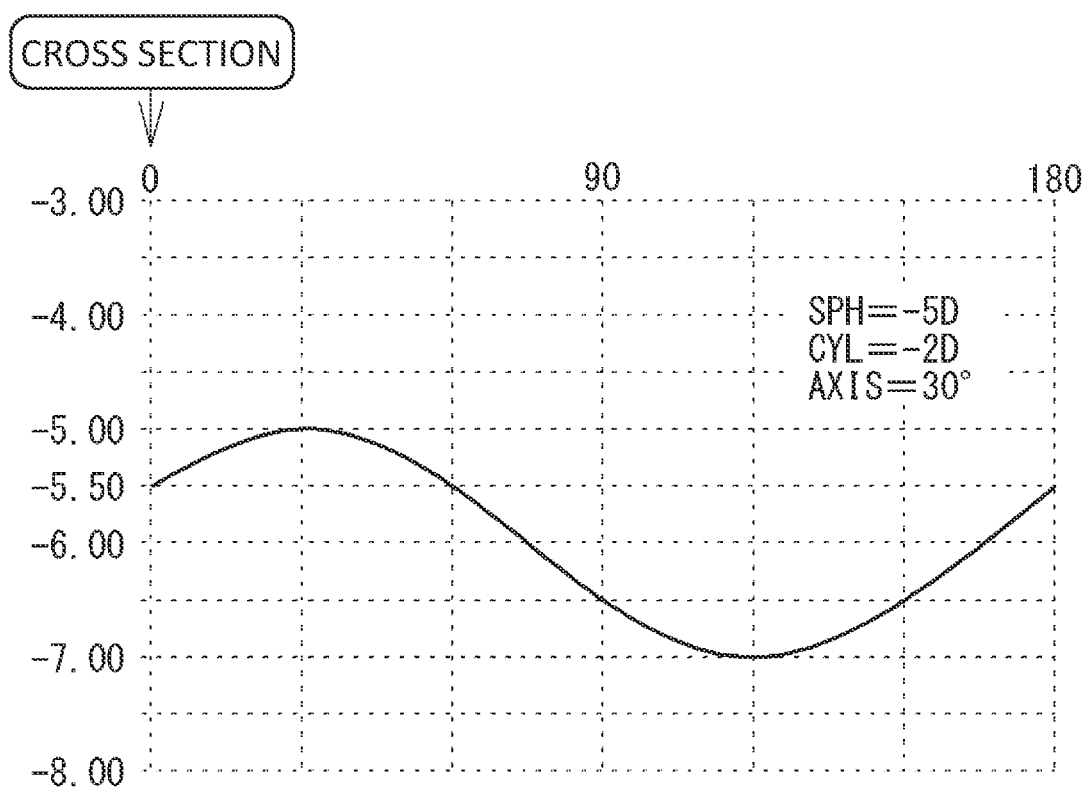
FIG. 5 is a flowchart illustrating an operation of the apparatus.

Next, the control operation of the ophthalmic apparatus 10 will be described with reference to a flowchart in FIG. 5.

In the present application example, the description will be made under the assumption that the ophthalmic apparatus 10 sequentially performs the corneal curvature measurement, capturing of the anterior segment cross-sectional image, and the eye refractive power measurement in an order, and then, the axial length is acquired based on the results of the measurement and imaging.

First, the position alignment of the measurement unit 11 with respect to the subject eye E is performed (S1). The examiner instructs the examinee to put his/her face on the face support unit 15. In addition, the display of the fixation target and the acquisition of the anterior segment observation image are started.

Thereafter, for example, the subject eye and the apparatus are adjusted to a predetermined positional relationship based on at least the observation image of the anterior segment acquired via the front imaging optical system 200. More specifically, the alignment in the XY direction is performed so that the optical axis L1 coincides with the corneal apex of the subject eye E. In addition, the alignment in the Z direction is performed so that the distance between the subject eye and the apparatus becomes a predetermined working distance. In this case, an alignment index (not illustrated) may be projected onto the cornea, and the alignment may be adjusted based on the alignment index detected in the observation image.

Next, the corneal shape is measured (S2). The pattern index is projected from the index projector 410 (index projection optical system 400), and the corneal Purkinje image of the pattern index is imaged by the front imaging optical system 200. The corneal shape information is acquired based on the corneal Purkinje image. The corneal shape information is derived based on the height of the corneal Purkinje image. In the present application example, at least each value of the corneal curvature, the astigmatic power, and the astigmatic axis angle is acquired as the corneal shape information.

Next, in the present application example, the eye refractive power is measured (S3). For example, the preliminary measurement may be performed first, and then the main measurement may be performed.

In the preliminary measurement, the eye refractive power of the subject eye E is measured in a state in which the fixation target is arranged at a predetermined display distance. At the time of measurement, a fixation target plate 155 may be placed at an initial position that is optically sufficient distance from the subject eye E and is corresponding to the far point of the OD eye. The ring image imaged by the image sensor element 125 based on the measurement light emitted in such a state is image-analyzed by the calculation controller 50. As a result of analysis, the value of refractive power in each meridian direction is obtained. By performing a predetermined processing on the refractive power in each meridian direction, at least the spherical power in the preliminary measurement is required.

Subsequently, the controller 50 moves the fixation target plate 155 to the fogging start position where the focal point of the subject eye E is focused according to the spherical power of the preliminary measurement of the subject eye E. As a result, the fixation target is clearly observed in the subject eye E. Thereafter, the controller 50 moves the fixation target from the fogging start position, and then, the controller 50 adds fogging to the subject eye E. As a result, the accommodation of subject eye E is released.

The main measurement is performed in a state in which fogging is added to the subject eye E. By performing a predetermined analysis processing on the ring image of the subject eye E to which fogging is added, the spherical power (SPH) of the subject eye, columnar power (CYL), and astigmatic axis angle objective values (AXIS) are acquired.

Next, a cross-sectional image of the anterior segment is captured (S4). In this case, the imaging operation is performed immediately after the main measurement of eye refractive power is completed. For example, the imaging operation of the cross-sectional image may be triggered by the completion of the main measurement of the eye refractive power. That is, immediately after the completion of the main measurement, the anterior segment is irradiated with the visible light emitted from the emission optical system 300a as the illumination light, and the cross-sectional image of the anterior segment imaged on the image sensor element 321 is acquired. Since the cross-sectional imaging of the anterior segment is performed immediately after the completion of the main measurement of the eye refractive power, the alignment deviation between the measurement of eye refractive power and the capturing of the cross-sectional image is reduced.

Furthermore, in the present application example, the anterior segment is not irradiated with the visible light before capturing the cross-sectional image, the occurrence of miosis is suppressed during the cross-sectional image shooting. As a result, a cross-sectional image in which the deeper part of the anterior segment is captured is more likely to be captured in a good condition.

Next, the calculation controller 50 calculates the axial length of the subject eye based on the information or the image acquired in each step of S2 to S4.

In the present application example, the axial length is derived based on the ray tracing techniques on the cross section.

Figure 6:
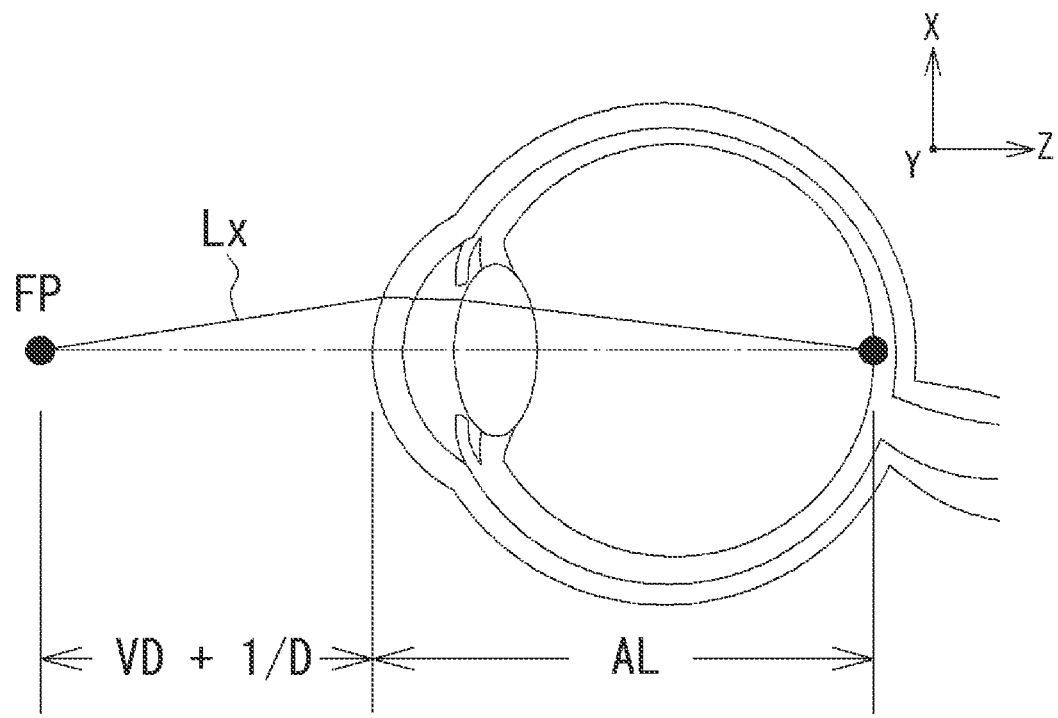
FIG. 6 is a schematic diagram illustrating a method for deriving the axial length by light beam tracing.

As illustrated in FIG. 6, the light beam incident on the subject eye from the far point FP (for example, light beam Lx in FIG. 6) is traced, and the position of the intersection point when the light beam is refracted by each ocular media of the subject eye and intersects with the optical axis is obtained. The distance between the obtained intersection point and the corneal apex is derived as the axial length. In the present application example, for the convenience of description, it is assumed that the refractive index of each ocular media (cornea, aqueous humor, and crystalline lens) is constant and there is no change in the refraction inside each body. However, the present disclosure is not necessarily limited thereto, and the axial length may be derived while taking the change in the refractive index inside the ocular media (for example, the change in the refractive index between the inside and outside of the crystalline lens) into consideration.

In addition, the refractive index information relating to the refractive index of the ocular media may be acquired separately from the cross-sectional image which is the anterior segment information, and then, the refractive index information may be used for deriving the axial length. That is, the refractive index of the ocular media based on the refractive index information may be further considered in acquiring the axial length. As for the refractive index information, for example, the refractive index of the crystalline lens is known to change with age. Therefore, the apparatus may include a calculation formula or a look-up table in which the refractive index of the crystalline lens is associated with each age. In this case, by inputting the age, the refractive index according to the age is required. The ray tracing techniques may be performed using this refractive index.

In this method, the following parameters are used in addition to the position of far point FP. The following parameters are acquired based on the Scheimpflug image and the corneal shape information.

Ra: Curvature radius of the front surface of the cornea
Rp: Curvature radius of the rear surface of the cornea
CT: Corneal thickness
ACD: Anterior chamber depth
ra: Curvature radius of the front surface of the crystalline lens
rp: Curvature radius of the rear surface of the crystalline lens
LT: Crystalline lens thickness In addition, the position of the far point FP of the subject eye from the corneal apex is obtained based on the result of measurement of the eye refractive power. For example, if the subject eye E has no astigmatism, SPH=−5D, and VD=12 mm, then the distance from the corneal apex to the far point FP is 12+1000/5=212 mm. It is considered that the light beam from here is imaged on the fundus of the subject eye. VD of 12 mm is a constant value indicating the distance between the corneal apexes under an assumption of wearing a spectacle. The VD can vary depending on the apparatus.

By the way, in the widely used expression format of the eye refractive power using SPH, CYL, and AXIS, since SPH indicates the refractive power for a strong main meridian (or a weak main meridian), the SPH value is not always an appropriate value for the light beam tracing on a cross section. For example, the case where SPH=−5D, CYL=−2D, and AXIS=30° can be considered. In this case, if the horizontal cross-section is acquired in the optical system described above as an example, the refractive power in this cross-section is neither −5D nor −7D where CYL is added.

On the other hand, in the present application example, the on-surface eye refractive power which is the eye refractive power on the cross section is obtained, and then, the position of far point FP is set based on the on-surface refractive power. Here, the refractivity in any surface is expressed by the following equation.

$$P(\theta)=S+C\times[\sin^2(\theta-A)]$$

However, θ is an angle with respect to the horizontal plane, and the horizontal direction is 0°. The cross section in the present application example is the horizontal plane (θ=0°). Therefore, when SPH=−5D, CYL=−2D, and AXIS=30°, then, P(0°) is calculated as −5.5D (refer to FIG. 7). In this case, 12+1000/5.5=194 mm is the distance from the corneal apex to the far point FP on the cross section.

Here, the light beam from the far point FP set in this way is traced. For example, a light beam (for example, the light beam Lx in FIG. 6) directed from the far point FP toward a certain position (as an example, φ6 mm position at the position of the pupil (about 3 mm deep from the cornea) of the subject eye) is guided. Setting a certain position 46 mm position at the position of the pupil of the subject eye is only an example, and can be changed as appropriate.

Firstly, the light beam undergoes the first refraction on the front surface of the cornea. The intersection point of the light beam and the front surface of the cornea is calculated is calculated based on the curvature radius Ra of the front surface of the cornea, the position of the far point FP, and the light beam angle at the far point FP. Further, the incident angle of the light beam at the intersection point is calculated. The light beam that reaches the front surface of the cornea changes the direction at a refraction angle fixed with respect to the incident angle based on the Snell's law. In this way, the light beams on the boundary surface of each ocular media are sequentially traced. At that time, various parameters (Ra, Rp, CT, ACD, ra, rp, and LT) acquired based on the Scheimpflug image and the corneal shape information are appropriately used to give an intersection point between each boundary surface and the light beam. In the present application example, a point of intersection with the eye axis (here, the visual axis) is obtained after finally exiting the rear surface of the crystalline lens. The distance from the intersection point to the corneal apex (here, the origin) is used as the axial length AL.

If the above-described various parameters (Ra, Rp, CT, ACD, ra, rp, LT) are used in the ray tracing techniques, in the present application example, for at least the curvature radius Ra of the front surface of the cornea, the value based on the corneal Purkinje image of the pattern index is used, and for the remaining values, the value based on the Scheimpflug image is used. That is because, in general, for the front surface of the corneal shape, the measurement accuracy based on the corneal Purkinje image is higher than the measurement accuracy based on the Scheimpflug image. As described above, in the present application example, at least the values of corneal curvature, astigmatic power, and astigmatic axis angle are acquired as the corneal shape information. Using a method similar to the method for obtaining the refractivity for the cross section, from these values, the corneal curvature (curvature of the front surface of the cornea) on the cross section can be obtained. The reciprocal of the obtained value is used as Ra.

As described above, the axial length can be obtained by tracing the light beam toward a certain position. However, the light beam tracing method is not limited to the above method. For example, a point to be imaged from the far point may be obtained by a paraxial calculation. In addition, a point to be imaged from the far point may be obtained while taking a plurality of light beams having different incident positions on the subject eye into consideration. For example, the light beam tracing for each light beam of the paraxial light beam and the light beam directed toward a certain position different from the paraxial, may be combined. When the light beam tracing of a plurality of light beams is performed, the final measurement value (calculated value) of the axial length may be the average value of the axial length by each light beam tracing (weighted average value). In addition, the axial length may be obtained by tracing the light beam toward the measurement region ($\varphi 2$ mm to $\varphi 4$ mm on the pupil) by the measurement optical system 100. For example, the light beam tracing may be performed on each of a plurality of light beams directed toward the region of $\varphi 2$ mm to $\varphi 4$ mm on the pupil, and the average value of the axial lengths obtained by each light beam tracing is acquired as the result of calculation. Since the light beam tracing is performed under more appropriate conditions, it is easier to acquire the axial length more accurately.

A predetermined offset value may be added to the axial length value obtained in the present application example. The offset value corrects the error between the calculated value and the measured value.

In addition, light beam tracing may be performed by tracing a light beam which is emitted from the far point and passes through a circumferential region on which a pattern index for measuring the corneal shape is projected. In this way, since the conditions for light beam tracing become more appropriate, the axial length is likely to be acquired more accurately.

The obtained axial length is displayed on the monitor 16. In the present application example, the axial length is displayed together with at least one of the eye refractive power (SPH, CYL, or AXIS) and the corneal shape information. If there exist past results of measurement for the subject eye, the current result of measurement may be displayed together with the past result of measurement of the axial length. For example, the result of measurement may be displayed by a trend graph in which the horizontal axis is the age (measurement date) and the vertical axis is the axial length. Of course, the display mode of the result of measurement is not limited to these.

Modification Example

As described above, the embodiment and the application example are described, however, the present disclosure is not limited to the above embodiment, and various modifications can be made.

For example, in the application example described above, for various parameters (Ra, Rp, CT, ACD, ra, rp, and LT) used for light beam tracing, the actually measured values are used. However, the present disclosure is not necessarily limited thereto, and standard values (hypothetical values) may be partially used for various parameters. The standard value may be an average value or a value adopted in a predetermined eye optical model (for example, a Gullstrand model eye model). A plurality of standard values may be prepared for at least any one of age, gender, and region, and which standard value should be used for obtaining the axial length may be selectable by the examiner.

In addition, for example, in the application example described above, the axial length of the subject eye is acquired as a result of calculation processing based on the eye refractive power and the anterior segment information of the subject eye. However, the present disclosure is not limited thereto, and the axial length may be acquired by using a mathematical model trained by a machine learning algorithm. A mathematical model refers, for example, to a data structure for predicting the relationship between the input data and the output data. The mathematical models are constructed by training using the training datasets. The training dataset is a set of input training data and output training data. The input training data is sample data input to the mathematical model. For example, as the input training data, the eye refractive power of a plurality of subject eyes acquired in the past and the anterior segment information are used. The output training data is sample data of values predicted by a mathematical model. For example, as the output training data, the axial length values of a plurality of subject eyes acquired in the past are used. The axial length value may be a measurement value acquired by an optical interference type or an ultrasonic type axial length measurement apparatus. The mathematical model is trained such that, when certain input training data is input, the corresponding output training data is output. In the present application example, the calculation controller may input the eye refractive power and the anterior segment information to the mathematical model, and then, the axial length value of the subject eye may be acquired as a predicted value.

In addition, for example, in the embodiment and the application example described above, the anterior segment information including information on the shape of the crystalline lens may be sequentially acquired while the fixation target is moved to add fogging. In this way, the shape change of the crystalline lens may be detected from the anterior segment information, and it may be confirmed whether or not the fogging is appropriately performed based on the shape change.

(1) An ophthalmic apparatus according to a second aspect of the present disclosure includes:
    a first optical system that irradiates a fundus of a subject eye with measurement light, the first optical system for acquiring information regarding an eye refractive power of the subject eye based on reflection light of the measurement light reflected from the fundus;

a second optical system for acquiring anterior segment information regarding a shape of an anterior segment, the anterior segment information including at least shape information of a crystalline lens;

a controller, wherein the controller controls the first optical system and the second optical system to acquire each of the information regarding the eye refractive power and the anterior segment information in a state where intraocular accommodations are identical each other, and the controller acquires an axial length of the subject eye based on the information regarding the eye refractive power and the anterior segment information which are acquired in the state where the intraocular accommodations are identical each other.

(2) In the ophthalmic apparatus according to the second aspect, the ophthalmic apparatus according to (1) described above further includes:

a fixation target display optical system that displays a fixation target, in which the controller controls an acquisition timing of each of the information regarding the eye refractive power and the anterior segment information such that accommodations for the subject eye by the fixation target are identical between an acquisition time of the information regarding the eye refractive power and an acquisition time of the anterior segment information.

(3) In the ophthalmic apparatus according to the second aspect, in the ophthalmic apparatus of (1) or (2) described above, the controller synchronizes acquisition timing of each of the information regarding the eye refractive power and the anterior segment information.

(4) In the ophthalmic apparatus according to the second aspect, in the ophthalmic apparatus according to (2) or (3) described above, the fixation target display optical system enables to change a display distance of the fixation target, and the controller perform fogging on the subject eye by controlling the fixation target display optical system, and acquires each of the information regarding the eye refractive power and the anterior segment information when the subject eye is in a fogged state.

(5) In the ophthalmic apparatus according to the second aspect, in the ophthalmic apparatus according to any one of (1) to (4) described above, the first optical system emits infrared light as the measurement light, and the second optical system includes an emission optical system that irradiates the anterior segment with slit light and a light receiving optical system including a lens system and an image sensor element that are arranged in a Scheimpflug relationship with respect to a cross section set in the anterior segment by the slit light, and acquires a cross-sectional image of the anterior segment based on a signal from the image sensor element.

(6) In the ophthalmic apparatus according to the second aspect, in the ophthalmic apparatus according to (5) described above, the second optical system emits visible light as the slit light, and the controller perform an acquisition operation of the information regarding the eye refractive power, and acquire the anterior segment information at a timing when the acquisition operation is completed.

(7) In the ophthalmic apparatus according to the second aspect, in the ophthalmic apparatus according to (5) or (6) described above, a light projection axis of the measurement light in the first optical system and a light projection axis of illumination light in the second optical system are arranged on an identical axis.

What is claimed is:

1. An ophthalmic apparatus comprising:

a first optical system that irradiates a fundus of a subject eye with measurement light, the first optical system for acquiring information regarding an eye refractive power of the subject eye based on reflection light of the measurement light reflected from the fundus;

a second optical system for acquiring anterior segment information regarding a shape of an anterior segment, the anterior segment information being related to a cross section on which an optical axis of the first optical system is arranged; and a calculation controller, wherein the calculation controller acquires an axial length of the subject eye based on an on-surface eye refractive power, which is the eye refractive power on the cross section, and the anterior segment information related to the cross section, wherein the cross section for acquiring the on-surface eye refractive power and the cross section for acquiring the anterior segment information is the same and the axial length of the subject eye is calculated from the on-surface eye refractive power and the anterior segment information that are acquired on the same cross section.

2. The ophthalmic apparatus according to claim 1, wherein the second optical system includes a cross-sectional imaging optical system that captures a cross-sectional image of the cross section set in the anterior segment of the subject eye, and the calculation controller acquires the axial length of the subject eye based on the on-surface eye refractive power and the anterior segment information which is based on the cross-sectional image.

3. The ophthalmic apparatus according to claim 2, wherein an imaged area of the cross-sectional image captured by the cross-sectional imaging optical system includes an area from a front surface of a cornea of the subject eye to at least a front surface of a crystalline lens.

4. The ophthalmic apparatus according to claim 2, further comprising:

a third optical system that includes an index projector which projects a pattern index for measuring a corneal shape to the anterior segment from a front face facing the subject eye, the third optical system capturing a corneal Purkinje image of the pattern index, and wherein the calculation controller acquires the axial length based on the on-surface eye refractive power, the anterior segment information, and corneal shape information which is based on the corneal Purkinje image.

5. The ophthalmic apparatus according to claim 1, wherein the anterior segment information is used for specifying at least two or more of a corneal thickness, a corneal front surface curvature radius, a corneal rear surface curvature radius, an anterior chamber depth, a crystalline lens thickness, a crystalline lens front surface curvature radius, and a crystalline lens rear surface curvature radius.

6. The ophthalmic apparatus according to claim 1,
wherein the calculation controller further acquires refractive index information regarding a refractive index of an ocular media in the subject eye, and
the calculation controller acquires the axial length of the subject eye while further taking the refractive index of the ocular media based on the refractive index information into consideration.

7. The ophthalmic apparatus according to claim 1,
wherein the anterior segment information includes information for specifying a shape of the anterior segment in a measurement region of the anterior segment for which the eye refractive power is measured by the first optical system, and
the calculation controller acquires the axial length based on the on-surface refractive power and the anterior segment information in the measurement region.

8. The ophthalmic apparatus according to claim 1,
wherein the calculation controller acquires the axial length while taking an eccentricity of an ocular media in the anterior segment which is specified by the anterior segment information.

9. The ophthalmic apparatus according to claim 1,
wherein the calculation controller controls the first optical system and the second optical system to acquire each of the information regarding the eye refractive power and the anterior segment information in a state where intraocular accommodations are identical each other, and
the calculation controller further acquires the axial length of the subject eye based on the eye refractive power and the anterior segment information which are acquired in the state where the intraocular accommodations are identical each other.

10. The ophthalmic apparatus according to claim 9, further comprising:
a fixation target display optical system that displays a fixation target,
wherein the calculation controller controls an acquisition timing of each of the information regarding the eye refractive power and the anterior segment information such that accommodations for the subject eye by the fixation target are identical between an acquisition time of the information regarding the eye refractive power and an acquisition time of the anterior segment information.

11. The ophthalmic apparatus according to claim 9,
wherein the calculation controller synchronizes acquisition timing of each of the information regarding the eye refractive power and the anterior segment information.

12. The ophthalmic apparatus according to claim 10,
wherein the fixation target display optical system enables to change a display distance of the fixation target, and
the calculation controller performs fogging on the subject eye by controlling the fixation target display optical system, and acquires each of the information regarding the eye refractive power and the anterior segment information when the subject eye is in a fogged state.

13. The ophthalmic apparatus according to claim 9,
wherein the first optical system emits infrared light as the measurement light, and
the second optical system includes an emission optical system that irradiates the anterior segment with slit light and a light receiving optical system including a lens system and an image sensor element that are arranged in a Scheimpflug relationship with respect to a cross section set in the anterior segment by the slit light, and acquires a cross-sectional image of the anterior segment based on a signal from the image sensor element.

14. The ophthalmic apparatus according to claim 13,
wherein the second optical system emits visible light as the slit light, and
the calculation controller performs an acquisition operation of the information regarding the eye refractive power, and acquires the anterior segment information at a timing when the acquisition operation is completed.

15. The ophthalmic apparatus according to claim 13,
wherein a light projection axis of the measurement light in the first optical system and a light projection axis of illumination light in the second optical system are arranged on an identical axis.

16. The ophthalmic apparatus according to claim 4,
wherein the index projector is arranged to avoid a light receiving optical axis in the second optical system.

17. The ophthalmic apparatus according to claim 16,
wherein the index projector projects the pattern index formed of a plurality of point images.

* * * * *